United States Patent [19]

Mizuchi et al.

[11] Patent Number: 5,358,945
[45] Date of Patent: Oct. 25, 1994

[54] PYRIMIDINE COMPOUND AND PHARMACEUTICALLY ACCEPTABLE SALTS THEREOF

[75] Inventors: Akira Mizuchi, Mobara; Ken Ikeda, Chiba; Yuichiro Kokubun; Kazutoshi Horikomi, both of Mobara; Tadayuki Sasaki, Funabashi; Akira Awaya, Yokohama; Ikuo Tomino, Yamaguchi; Masaharu Ishiguro, Yamaguchi; Takumi Kitahara, Yamaguchi; Noriaki Kihara, Yamaguchi, all of Japan

[73] Assignees: Mitsui Petrochemical Industries, Ltd.; Mitsui Pharmaceuticals, Inc., both of Tokyo, Japan

[21] Appl. No.: 836,283

[22] PCT Filed: Jul. 3, 1991

[86] PCT No.: PCT/JP91/00898

§ 371 Date: Mar. 30, 1992

§ 102(e) Date: Mar. 30, 1992

[87] PCT Pub. No.: WO92/00970

PCT Pub. Date: Jan. 23, 1992

[30] Foreign Application Priority Data

Jul. 3, 1990 [JP] Japan .................................. 2-176077

[51] Int. Cl.$^5$ .................. C07D 239/48; C07D 401/02; C07D 401/14; A61K 31/505
[52] U.S. Cl. .................. 514/227.8; 514/235.8; 514/228.2; 514/275; 514/252; 544/58.5; 544/295; 544/60; 544/62; 544/122; 544/324; 544/323
[58] Field of Search .................. 544/295, 60, 62, 122, 544/324, 323, 58.5; 514/235.8, 227.8, 228.2, 275, 252

[56] References Cited

PUBLICATIONS

Campbell et al, Chemical Abstracts, vol. 97, entry 2/6224b (1982).
Abraham et al., Chemical Abstracts, 70:76976p (1969).
Geerts et al., Chemical Abstracts, 80:107548p (1974).
Naar et al, Chemical Abstracts, 83:43369h (1975).
Warczykowska et al, Chem. Abstracts, 94:3979c (1981).
Fujiwara et al., Chem. Abstracts, 107:198362p (1987).
Tomino et al., Chem. Abstracts, 114:23983j (1991).

*Primary Examiner*—John M. Ford
*Attorney, Agent, or Firm*—Sherman and Shalloway

[57] ABSTRACT

The present invention relates to pyrimidine compounds represented by the formula

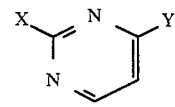

(wherein X is a substituted or a cyclic amino group and Y is a substituted amino group or a substituted carbonyl group) or their pharmaceutically acceptable salts, and a therapeutic agent for neurological diseases comprising the compounds.

These compounds are useful for treatment of various disorders in nervous systems since they are effective on growth of neurons and promotion of the formation and elongation of neutrites.

4 Claims, No Drawings

PYRIMIDINE COMPOUND AND PHARMACEUTICALLY ACCEPTABLE SALTS THEREOF

FIELD OF THE INVENTION

This invention relates to novel pyrimidines or their pharmaceutically acceptable salts thereof, and novel therapeutic agents for neurological diseases of the peripheral and central nervous systems of animals containing the above compounds as active ingredients.

PRIOR ART

Japanese Patent Publication No. 23,394/1971 discloses that aminopyrimidines represented by the following formula

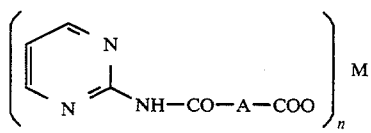

wherein A represents an alkylene group having up to 16 carbon atoms, or a lower alkylene group substituted by an amino group or $C_{2-5}$ acylamino group, M represents H, Na, K, $NH_4$, Mg, Ca or an organic basic ammoniun salt, and n is a value equal to the atomic valency of M, have interesting therapeutic activity, particularly as an anti-melanchoric agent and psychoanaleptic agent in the filed of psychosis. Japanese Laid-Open Patent Publication No. 22044/1976 discloses that dichloro-lower aliphatic carboxylic acid salts of 2-isopropylaminopyrimidine, such as 2-isopropylaminopyrimidine dicloroacetate, are useful as a therapeutic agent for a neurological disease. Japanese Laid-Open Patent Publication No. 100477/1977 (Patent Publication No. 28548/1984) discloses that 2-isopropylaminopyrimidine phosphate is useful as a therapeutic agent for a neurological disease. Japanese Laid-Open Patent Publication No. 157575/1979 discloses a process for producing 2-chloropyrimidine in a high yield. A working example in this patent publication describes the preparation of 2-chloropyrimidine in a yield of 69%. Japanese Laid-Open Patent Publication No. 393/1980 discloses a process for producing 2-isopropylamino-pyrimidine in a high yield. A working example of this patent publication describes the preparation of 2-isopropylaminopyrimidine in a yield of 60%.

Japanese Laid-Open Patent Publication No. 122768/1980 discloses that a hydroxy derivative of 2-isopropylaminopyrimidine represented by the following formula

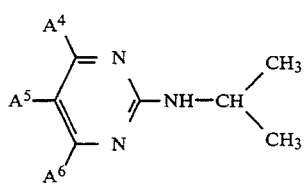

wherein $A^4$, $A^5$ and $A^6$ each represent H or OH, and at least one of them represents OH, is useful in the field of nerve regeneration and for treatment of myodystrophy.

Japanese Laid-Open Patent Publication No. 145670/1980 discloses that 2-isopropylaminohalogenopyrimidines represented by the following formula

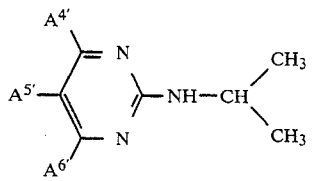

wherein $A^{4'}$, $A^{5'}$ and $A^{6'}$ each represent H or a halogen atom, and at least one of them is a halogen atom, are useful for treatment of various neurological diseases and myodystrophy.

Japanese Laid-Open Patent Publication No. 145,671/1980 discloses a process for producing a hydroxy derivative of 2-isopropylaminopyrimidine. Japanese Laid-Open Patent Publication No. 151,571/1980 discloses that 2-isopropylamino-5-halogenopyrimidines are interesting in the treatment of neurological diseases.

Japanese Laid-Open Patent Publication No. 10177/1981 discloses a process for producing 2-isopropylaminopyrimidine substantially in a quantitative yield by aminolyzing 2-methylsulfornylpyrimidine with isopropylamine.

Japanese Laid-Open Patent Publication No. 26880/1981 discloses a process for producing 2-isopropylaminopyrimidine which comprises reacting bis (isopropylguanidine) sulfate with 1,1,3,3-tetraethoxypropane.

Japanese Laid-Open Patent Publication No. 90,013/1981 describes a therapeutic agent for myodystropy, myopathy, muscle rigidity and/or dysfunction of neuro-musclar transmission comprising substituted derivative of pyrimidine or its therapeutically acceptable salt of its metabolite as an active ingredient. However, it merely discloses various salts such as an or 2-isopropylaminopyrimidine orthophosphate as an active compound.

Japanese Laid-Open Patent Publication No. 65873/1986 discloses that 2-piperazinopyrimidine derivatives of the following formula

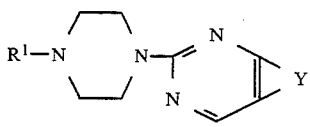

wherein $R^1$ is H or aralkyl, and Y is a divalent organic group defined in the claim of this patent publication are useful as a herbicide for paddies and upland farms.

The present inventors previously provided a novel therapeutic agent for neurological diseases comprising a specified 2-piperazinopyrimidine derivative or its pharmaceutically acceptable salt (International Laid-Open No. WO87/04928, Japanese Patent Application No. 41729/1989, Japanese Patent Application No. 334759/1989).

PROBLEMS TO BE SOLVED BY THE INVENTION

It is an object of this invention to provide novel pyrimidines and their pharmaceutically acceptable salts. Another object of this invention is to provide therapeutic agents for neurological diseases comprising the above novel compounds.

Another object of this invention is to provide a novel therapeutic agent for neurological diseases having the effect of regeneration and repairing nerve cells.

Another object of this invention is to provide a novel therapeutic agent for neurological diseases which can be applied to disorders of peripheral nerves and spinal injuries.

Another object of this invention is to provide a novel therapeutic agent for neurological diseases which can be applied to diseases of central nerves which are different from psycosis and in which abnormality, in the operating system or the metabolic system of chemical transmitters is regarded to be primarily involved.

Another object of this invention is to provide a novel therapeutic agent for cerebral diseases which has the effect of improving and restoring learning and memory.

Another object of this invention is to provide a novel therapeutic agent for neurological diseases or cerebral diseases, which comprises a comprehensively excellent and useful compound having pharmacological actions suitable for treatment of neurological diseases or cerebral diseases with little side effects such as liver disorder.

Still other objects of this invention along with its advantages will become apparent from the following description.

MEANS FOR SOLVING THE PROBLEM

The present invention provides a pyrimidine compound represented by the following formula (I)

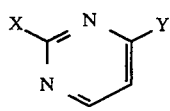 (I)

{wherein X is selected from the group consisting of;

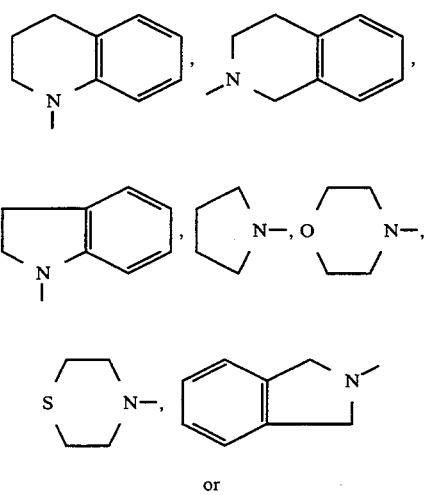

or

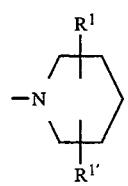

(wherein $R^1$, $R^{1'}$ maybe the same or different and represents a hydrogen atom, a lower alkyl group, a benzyl group, a phenyl group or a lower alkoxycarbonyl group),

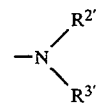

(wherein $R^{2'}$ and $R^{3'}$ represents a lower alkyl group) or

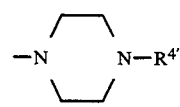

(wherein $R^{4'}$ is a hydrogen atom, a lower alkyl group, a phenyl group or a benzyl group) and Y represents

[wherein $R^2$ is a hydrogen atom or a lower alkyl group and $R^3$ is a lower acyl group,

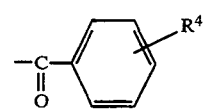

(wherein $R^4$ is a hydrogen atom, or a trifluoromethyl group, a hydroxyl group, a cyano group, a formyl group, a lower acyl group, a lower alkoxycarbonyl group, or a fluorosulfonyl group),

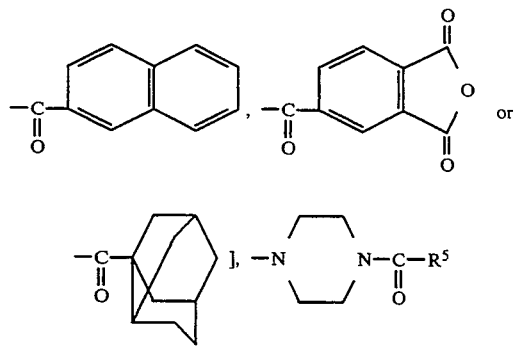

(wherein $R^5$ is a hydrogen atom, a lower alkyl group or a phenyl group),

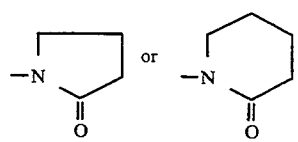

provided that when Y is and R³ is a lower acyl group or $$-\underset{\underset{O}{\|}}{C}-\phantom{l}\text{phenyl},$$

X is selected from the group consisting of;

indoline, isoindoline or thiomorpholine or their pharmaceutically acceptable salts.

In addition, the present invention provides therapeutic agents for neurological diseases containing the compounds of the formula (I) or their pharmaceutically acceptable salts as active ingredients. The compounds of the above formula (I) of the present invention may be produced by methods known in the art, specifically the methods described in Japanese Patent Publication No. 140568/1986 and No. 87627/1986, or by treating the intermediates obtained by the methods described above by methods known in the art (e.g., reductive elimination of a protecting group). The examples 1–3 described below will illustrate a process for producing each compound in detail.

For example, when compounds of the formula (I) wherein Y is—NR²R³ and R² is a lower alkyl group are attempted to be produced, the compounds can be produced by the following Reaction Sheme 1.

Reaction Sheme 1

$$X\underset{N}{\overset{N}{\diagdown}}NHR^2 + R^3-Cl \longrightarrow X\underset{N}{\overset{N}{\diagdown}}NR^2R^3$$

(II)

The source of the compound (II) of the Reaction Sheme 1 is produced using a starting material, $$Cl\underset{N}{\overset{N}{\diagdown}}Cl$$

according to the method described in J. Chem. Soc., 1965, p755–761. The reaction of the Reaction Sheme 1 is preferably carried out in solvents such as toluene, dioxane, pyridine or water at 20° C.–150° C. and, if necessary, in the presence of basic compounds. Suitable basic compounds include organic bases such as triethylamine, pyridine and 4-dimethylaminopyridine and inorganic bases such as sodium carbonate and potassium carbonate.

Compounds of the formula (I) wherein X is $$-N\diagup\diagdown\underset{R^{1'}}{\overset{R^1}{\diagdown}}$$

and Y is $$-N\diagup\diagdown N-\underset{\underset{O}{\|}}{C}-R^5$$

may be produced by reacting, for example, carbonyl chlorides having a structural formula $$R^5-\underset{\underset{O}{\|}}{C}-Cl$$

with compounds having the following structural formula $$X\underset{N}{\overset{N}{\diagdown}}\underset{}{\overset{}{\diagdown}}N\diagup\diagdown NH$$

which are generated from a starting material, 2, 4-dichloropyrimidine.

Compounds of the formula (I) wherein Y is pyrrolidinone or piperidinone may be produced by the following Reaction Scheme2.

Reaction Scheme 2

$$X\underset{N}{\overset{N}{\diagdown}}Cl + H_2N-(CH_2)_n-COOH \longrightarrow$$
$$n = 3, 4$$

(III)

$$X\underset{N}{\overset{N}{\diagdown}}NH-(CH_2)_n-COOH$$

(IV)

-continued
Reaction Scheme 2

(IV) + SOCl₂ ⟶ 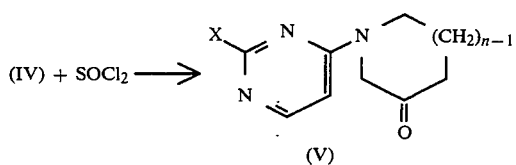

(V)

The reaction to synthesize the compounds (IV) in the Reaction Scheme 2 may be preferably carried out in solvents such as isopropanol, n-butanol, n-pentanol, isopentanol at 60°–200 °C. and, if necessary, in the presence of basic compounds. Suitable basic compounds include organic bases such as triethylamine, pyridine and 4-dimethylaminopyridine and inorganic bases such as sodium carbonate and potassium carbonate. The reaction to synthesize the compound(V) may be preferably carried out in the absence or presence of solvents, e.g., methylene chloride, chloroform, ethylenedichloride and toluene at 0 °C.-100 °C.

A process of producing the compounds (I) and salts thereof of the present invention may be described in the Examples in detail. The typical compounds (I) and salts thereof of the present invention are listed in Table 1. In the Table 1, the abbreviation listed under a "salts" column, the right side of the Table, represents the following:

- -: free compounds
- PTSOH: p-toluenesulfonate
- MALEATE: Maleate

TABLE 1

| Comp. No. | | Salts |
|---|---|---|
| 100 | [structure] | — |
| 104 | [structure] | PTSOH |
| 108 | [structure] | — |
| 112 | [structure] | PTSOH |
| 116 | [structure] | — |
| 120 | [structure] | PTSOH |
| 124 | [structure] | — |
| 128 | [structure] | PTSOH |

TABLE 1-continued

| Comp. No. | Salts |
|---|---|
| 132 | — |
| 136 | PTSOH |
| 140 | — |
| 144 | PTSOH |
| 148 | — |
| 152 | PTSOH |
| 156 | — |
| 160 | PTSOH |
| 164 | — |
| 168 | PTSOH |

TABLE 1-continued

| Comp. No. | Structure | Salts |
|---|---|---|
| 172 | (4-phenylpiperidin-1-yl)-pyrimidin-4-yl, N-CH₃, N-CO-C₆H₄-COCH₃ | — |
| 176 | (4-phenylpiperidin-1-yl)-pyrimidin-4-yl, N-CH₃, N-CO-C₆H₄-COCH₃ | PTSOH |
| 180 | (isoindolin-2-yl)-pyrimidin-4-yl, N-CH₃, N-CO-C₆H₅ | — |
| 184 | (isoindolin-2-yl)-pyrimidin-4-yl, N-CH₃, N-CO-C₆H₅ | PTSOH |
| 188 | (piperidin-1-yl)-pyrimidin-4-yl, N-CH₃, N-CO-C₆H₄-COOCH₃ | — |
| 192 | (piperidin-1-yl)-pyrimidin-4-yl, N-CH₃, N-CO-C₆H₄-COOCH₃ | MALEATE |
| 196 | (piperidin-1-yl)-pyrimidin-4-yl, N-CH₃, N-CO-C₆H₄-CHO | — |
| 200 | (piperidin-1-yl)-pyrimidin-4-yl, N-CH₃, N-CO-C₆H₄-CHO | MALEATE |
| 204 | (piperidin-1-yl)-pyrimidin-4-yl, N-CH₃, N-CO-C₆H₄-COCH₃ | — |
| 208 | (piperidin-1-yl)-pyrimidin-4-yl, N-CH₃, N-CO-C₆H₄-COCH₃ | MALEATE |
| 212 | (thiomorpholin-4-yl)-pyrimidin-4-yl, N-CH₃, N-COCH₃ | — |

TABLE 1-continued

| Comp. No. | | Salts |
|---|---|---|
| 216 | (thiomorpholine)-C(=N)-pyrimidine-N(CH₃)COCH₃ | MALEATE |
| 220 | (piperidine)-C(=N)-pyrimidine-piperazine-N-CHO | — |
| 224 | (piperidine)-C(=N)-pyrimidine-piperazine-N-CHO | MALEATE |
| 228 | (piperidine)-C(=N)-pyrimidine-piperazine-N-CO-phenyl | — |
| 232 | (piperidine)-C(=N)-pyrimidine-piperazine-N-CO-phenyl | MALEATE |
| 236 | (piperidine)-C(=N)-pyrimidine-piperazine-N-COCH₃ | — |
| 240 | (piperidine)-C(=N)-pyrimidine-piperazine-N-COCH₃ | MALEATE |
| 244 | (4-phenylpiperidine)-C(=N)-pyrimidine-piperazine-N-CO-phenyl | — |
| 248 | (4-phenylpiperidine)-C(=N)-pyrimidine-piperazine-N-CO-phenyl | MALEATE |
| 252 | (4-phenylpiperidine)-C(=N)-pyrimidine-piperazine-N-COCH₃ | — |
| 256 | (4-phenylpiperidine)-C(=N)-pyrimidine-piperazine-N-COCH₃ | MALEATE |

TABLE 1-continued

| Comp. No. | Salts |
|---|---|
| 260 | — |
| 264 | MALEATE |
| 268 | — |
| 272 | PTSOH |
| 273 | MALEATE |
| 274 | HCl |
| 276 | — |
| 280 | PTSOH |
| 284 | — |
| 288 | PTSOH |
| 292 | — |

TABLE 1-continued

| Comp. No. | | Salts |
|---|---|---|
| 296 | [structure: 4-phenylpiperidine-N-C(=N)-pyrimidine-N-(2-oxopiperidine)] | PTSOH |
| 300 | [structure: 4-methylpiperidine-N-C(=N)-pyrimidine-N-(2-oxopyrrolidine)] | — |
| 304 | [structure: 4-methylpiperidine-N-C(=N)-pyrimidine-N-(2-oxopyrrolidine)] | PTSOH |
| 308 | [structure: 4-ethylpiperidine-N-C(=N)-pyrimidine-N-(2-oxopyrrolidine)] | — |
| 312 | [structure: 4-ethylpiperidine-N-C(=N)-pyrimidine-N-(2-oxopyrrolidine)] | PTSOH |
| 316 | [structure: pyrrolidine-N-C(=N)-pyrimidine-N-(2-oxopyrrolidine)] | — |
| 320 | [structure: pyrrolidine-N-C(=N)-pyrimidine-N-(2-oxopyrrolidine)] | HCl |
| 324 | [structure: 2-methylpiperidine-N-C(=N)-pyrimidine-N-(2-oxopyrrolidine)] | — |
| 328 | [structure: 2-methylpiperidine-N-C(=N)-pyrimidine-N-(2-oxopyrrolidine)] | HCl |
| 332 | [structure: 3-methylpiperidine-N-C(=N)-pyrimidine-N-(2-oxopyrrolidine)] | — |

TABLE 1-continued

| Comp. No. | Structure | Salts |
|---|---|---|
| 336 | 3-methylpiperidinyl-C(=N-)-N(pyrrolidinone)-CH=CH-N= | HCl |
| 340 | 3,5-dimethylpiperidinyl-C(=N-)-N(pyrrolidinone)-CH=CH-N= | — |
| 344 | 3,5-dimethylpiperidinyl-C(=N-)-N(pyrrolidinone)-CH=CH-N= | HCl |
| 348 | 1,2,3,4-tetrahydroisoquinolin-2-yl-C(=N-)-N(pyrrolidinone)-CH=CH-N= | — |
| 352 | 1,2,3,4-tetrahydroisoquinolin-2-yl-C(=N-)-N(pyrrolidinone)-CH=CH-N= | HCl |
| 356 | 1,2,3,4-tetrahydroquinolin-1-yl-C(=N-)-N(pyrrolidinone)-CH=CH-N= | — |
| 360 | 1,2,3,4-tetrahydroquinolin-1-yl-C(=N-)-N(pyrrolidinone)-CH=CH-N= | HCl |
| 364 | 4-benzylpiperidinyl-C(=N-)-N(pyrrolidinone)-CH=CH-N= | — |
| 368 | 4-benzylpiperidinyl-C(=N-)-N(pyrrolidinone)-CH=CH-N= | HCl |

TABLE 1-continued

| Comp. No. | Structure | Salts |
|---|---|---|
| 372 | H5C2O-C(=O)-[piperidine]-N-[pyrimidine]-N-[pyrrolidinone] | — |
| 376 | H5C2O-C(=O)-[piperidine]-N-[pyrimidine]-N-[pyrrolidinone] | HCl |
| 380 | HN-[piperazine]-N-[pyrimidine]-N-[pyrrolidinone] | — |
| 384 | HN-[piperazine]-N-[pyrimidine]-N-[pyrrolidinone] | HCl |
| 388 | O-[morpholine]-N-[pyrimidine]-N-[pyrrolidinone] | — |
| 392 | O-[morpholine]-N-[pyrimidine]-N-[pyrrolidinone] | HCl |
| 396 | S-[thiomorpholine]-N-[pyrimidine]-N-[pyrrolidinone] | — |
| 400 | S-[thiomorpholine]-N-[pyrimidine]-N-[pyrrolidinone] | HCl |
| 404 | H3C-N-[piperazine]-N-[pyrimidine]-N-[pyrrolidinone] | — |
| 408 | H3C-N-[piperazine]-N-[pyrimidine]-N-[pyrrolidinone] | HCl |

TABLE 1-continued

| Comp. No. | | Salts |
|---|---|---|
| 412 | (structure) | — |
| 416 | (structure) | HCl |
| 420 | (structure) | — |
| 424 | (structure) | HCl |
| 428 | (structure) | — |
| 432 | (structure) | HCl |
| 436 | (structure) | — |
| 440 | (structure) | HCl |

Investigations of the present inventors show that the compounds of formula (I) provided by this invention have been found to be useful as therapeutic agents for neurological diseases.

The compounds of formula (I) are used normally in the form of a pharmaceutical composition, and administered through various routes, for example oral, subcutaneous, intramuscular, intravenous, intrarhinal, skin permeation and intrarectal routes.

The present invention also includes a pharmaceutical composition comprising a pharmaceutically acceptable carrier and a compound of general formula (I) or its pharmaceutically acceptable salt as an active ingredient. The pharmaceutically acceptable salt includes, for example, acid addition salts and quaternary ammonium (or amine) salts.

Examples of the pharmaceutically acceptable salts of the compounds (I) include salts formed from acids capable of forming pharmaceutically acceptable non-toxic acid-addition salts containing anions, such as hydrochlorides, hydrobromides, sulfates, bisulfites, phosphates, acid phosphates, acetates, maleates, fumarates, succinates, lactates, tartrates, benzoates, citrates, gluconates, glucanates, methanesulfonates, p-toluenesulfonates and naphthalanesulfonates or their hydrates, and quaternary ammonium (or amine) salts or their hydrates.

The composition of this invention may be formulated into tablets, capsules, powders, granules, troches, cachet wafer capsules, elixirs, emulsions, solutions, syrups, suspensions, aerosols, ointments, aseptic injectable, molded cataplasmas, soft and hard gelatin capsules, suppositories, and aseptic packed powders. Examples of the pharmaceutically acceptable carrier include lactose, glucose, sucrose, sorbitol, mannitol, corn starch, crystalline cellulose, gum arabic calcium phosphate, alginates, calcium silicate, microcrystalline cellulos, polyvinyl pyrrolidone, tragacanth gum, gelatin, syrup, methyl cellulose, carboxymethyl cellulose, methylhydroxybenzoic acid esters, propylhydroxybenzoic acid esters, talc, magnesium stearates, inert polymers, water and mineral oils.

Both solid and liquid compositions may contain the aforesaid fillers, binders, lubricants, wetting agents, disintegrants, emulsifying agents, suspending agents, preservatives, sweetening agents and flavoring agents. The composition of this invention may be formulated such that after administration to a patient, the active compound is released rapidly, continuously or slowly.

In the case of oral administration, the compound of formula (I) is mixed with a carrier or diluent and formed into tablets, capsules, etc. In the case of parenteral administration, the active ingredient is dissolved in a 10% aqueous solution of glucose, isotonic salt water, sterlized water or a like liquid, and enclosed in vials or ampoules for intravenous instillation or injection or intramuscular injection. Advantageously, a dissolution aid, a local anesthetic agent, a preservative and a buffer may also be included into the medium. To increase stability, it is possible to lyophilize the present composition after introduction into a vial or ampoule. Another example of parenteral administration is the administration of the pharmaceutical composition through the skin as an ointment or a cataplasm. In this case, a molded cataplasm or a tape is advantageous.

The composition of this invention contains 0.1 to 2000 rag, more generally 0.5 to 1000 mg, of the active component for each unit dosage form.

The compound of formula (I) is effective over a wide dosage range. For example, the amount of the compound administered for one day usually falls within the range of 0.03 mg/kg to 100 mg/kg. The amount of the compound to be actually administered is determined by a physician depending, for example, upon the type of the compound administered, and the age, body weight, reaction, condition, etc. of the patient and the administration route.

The above dosage range, therefore, does not limit the scope of the invention. The suitable number of administrations is 1 to 6, usually 1 to 4, daily.

The compound of formula (I) by itself is an effective therapeutic agent for disorders of the periphral nervous system and the central nervous system. If required, it may be administered in combination with at least one other equally effective drug. Examples of such an additional drug are gangliosides, mecobalamin and isaxonine.

The formulations of the compounds (I) in accordance with this invention and their biological activities will be illustrated in detail by a series of Examples given below. It should be understood however that they do not limit the scope of the invention. Each of the following examples showing the composition of the invention uses one of the compounds described hereinabove or one of other pharmaceutically active compounds encompassed within general formula (I)

EXAMPLE

Example 1

4-(N-methyl-4-trifluoromethyl benzoylamino)-2-(4-phenylpiperidino) pyrimidine (compound No. 108)

10 ml of tetrahydrofuran solution containing 1.0 g of 4-trifluoromethylbenzoylchloride (4.8 mM) was added to 30 ml of tetrahydrofuran solution containing 1.1 g of 4-methylamino-2-(4-phenylperidino) pyrimidine (4raM) and 2 ml of triethylamine over a period of 30 minutes at room temperature. The mixture was stirred for 12 hours. Water and dichloromethane were added to the reaction mixture.

The organic layer was separated, dried with sodium sulfate anhydride and concentrated under reduced pressure. The concentrate was purified by a solica gel chromatography to give a desired product, an oil-like substance (1.6 g, yield 83%).

$^1$H-NMR spectrum (deuterochloroform, δ ppm) 1.2–1.9 (4H, m), 2.5–2.9 (3H, m), 3.52 (3H, s), 4.48 (2H, hr. d, J=12Hz), 6.14 (1H, d, J=7Hz), 7.1–7.4 (SH, m), 7.56 (4H, s), 8.12 (1H, d, J=7Hz)

Compounds produced by the same method as described above and their physical properties are listed in Table 2.

TABLE 2

| Comp. No. | Yield (%) | $^1$H-NMR spectrum (CDCl$_3$ solution, δ ppm) |
|---|---|---|
| 100 | 86 | 3.12(2H, t, J=8Hz), 3.63(3H, s), 4.06(2H, t, J=8Hz), 6.34(1H, d, J=7Hz) 6.8–7.6(9H, m), 8.10(1H, d, J=7Hz) |
| 116 | 80 | 1.1–1.9(4H, m), 2.5–2.9(3H, m), 3.52(3H, s), 3.83(3H, s), 4.48(2H, br, d, J=12Hz), 6.14(1H, d, J=7Hz), 7.0–7.4(5H, m), 7.46(2H, d, J=8Hz), 7.98(2H, d, J=8Hz), 8.08(1H, d, J=7Hz) |
| 124 | 76 | 1.2–2.0(4H, m), 2.5–2.9(3H, m), 3.50(3H, s), 4.46(2H, br, d, J=12Hz), 6.14(1H, d, J=7Hz), 7.0–7.4(5H, m), 7.4–7.7(4H, m), 8.12(1H, d, J=7Hz) |
| 132 | 68 | 1.2–1.9(4H, m), 2.4–2.9(3H, m), 3.52(3H, s), 4.38(2H, br, d, J=12Hz), 6.10(1H, d, J=7Hz), 7.0–7.4(5H, m), 7.62(2H, d, J=8Hz), 7.94(2H, d, J=8Hz), 8.16(1H, d, J=7Hz) |
| 140 | 71 | 1.1–1.7(4H, m), 2.4–2.8(3H, m), 3.55(3H, s), 4.44(2H, br, d, J=12Hz), 6.06(1H, d, J=7Hz), 6.9–7.9(12H, m), 7.98(1H, d, J=7Hz) |
| 148 | 63 | 1.1–1.9(4H, m), 2.5–3.0(3H, m), 3.54(3H, s), 4.52(2H, br, d, J=12Hz), 6.18(1H, d, J=7Hz), 7.0–7.4(5H, m), 7.58(2H, d, J=8Hz), 7.84(2H,d J=8Hz), 8.13(1H, d, J=7Hz), 9.98(1H, s) |
| 156 | 47 | 1.5–3.2(20H, m), 3.24(3H, s), 4.92(2H, m), 6.35(1H, d, J=7Hz), 7.23(5H, m), 8.23(1H, d, J=7Hz) |
| 164 | 45 | 1.1–2.9(7H, m), 3.57(3H, s), 4.40(2H, m), 6.1–8.7(10H, m) |
| 172 | 80 | 1.3–2.0(m, 4H), 2.02(s, 3H), 2.5–3.0(m, 3H), 3.02(s, 3H), 4.6–5.0(m, 2H), 5.92(d, 1H, J=7Hz), 7.0–7.4(m, 9H), 8.04(d, 1H, J=7Hz) |
| 180 | 40 | 3.68(3H, s), 4.10(2H, s), |

TABLE 2-continued

| Comp. No. | Yield (%) | ¹H-NMR spectrum (CDCl₃ solution, δ ppm) |
|---|---|---|
| 188 | 92 | 4.58(2H, s), 6.06(1H, d, J=7Hz), 7.2–7.6(9H, m), 8.10(1H, d, J=7Hz) 1.1–1.8(6H, m), 3.06(s, 3H), 3.0–3.6(4H, m), 3.80(s, 3H), 6.10(d, 1H, J=7Hz), 7.90(d, 1H, J=7Hz), 7.43(d, 2H, J=7Hz), 7.76(d, 2H, J=7Hz) |
| 196 | 72 | 1.1–1.8(m, 6H), 3.47(s, 3H), 3.0–3.5(m, 4H), 6.15(1H, d, J=7Hz), 8.09(d, 1H, J=7Hz), 7.55(d, 2H, J=7Hz), 7.80(d, 2H, J=7Hz), 9.93(s, 1H) |
| 204 | 83 | 1.2–1.7(m, 6H), 2.04(s, 3H), 3.08(s, 3H), 3.0–3.5(m, 4H), 5.93(d, 1H, J=7Hz), 8.03(d, 1H, J=7Hz), 7.0–7.4(m, 4H) |
| 212 | 37 | 2.32(3H, s), 2.64(4H, m), 3.36(3H, s), 4.12(4H, m), 6.63(1H, d, J=7Hz), 8.23(1H, d, J=7Hz) |
| 220 | 82 | 1.62(6H, br, s), 3.3–4.0(12H, m), 5.92(1H, d, J=7Hz), 7.88(1H, d, J=7Hz), 8.10(1H, s) |
| 228 | 75 | 1.62(6H, br, s), 3.5–3.9(12H, m), 5.82(1H, d, J=7Hz), 7.44(5H, s), 7.98(1H, d, J=7Hz) |
| 236 | 65 | 1.64(6H, br, s), 2.16(3H, s), 3.4–3.9(12H, m), 5.80(1H, d, J=7Hz), 7.94(1H, d, J=7Hz) |
| 244 | 81 | 1.2–2.1(4H, m), 2.5–3.1(3H, s), 3.64(8H, br, s), 4.86(2H, br, s, J=8Hz), 5.84(1H, d, J=7Hz), 7.1–7.4(5H, m), 7.38(5H, s), 7.98(1H, d, J=7Hz) |
| 260 | 86 | 1.4–2.1(4H, m), 2.6–3.2(3H, m), 3.54(3H, s), 4.70(2H, br. d, J=12Hz), 7.2–7.4(5H, m), 7.38(2H, d, J=8Hz), 8.00(1H, d, j=7Hz) |
| 252 | 84 | 1.4–2.0(4H, m), 2.12(3H, s), 2.5–3.1(3H, m), 3.4–3.8(8H, m), 4.90(2H, br. s, d, J=12Hz), 5.84(1H, d, J=7Hz), 7.1–7.4(5H, m), 7.98(1H, d, J=7Hz) |

Example 2

4-(N-methyl-4-trifluoromethylbenzoylamino)-2-(4-phenylpiperidino) pyrimidine p-toluenesulfonate (compound No. 112)

30 ml of ethyl acetate containing 0.63g of p-toluenesulfonic acid hydrate(3.3 mM) was added to 10 ml of ethyl acetate containing 1.45g of 4-(N-methyl-4-trifluoro-methylbenzoyl amino)-2-(4-phenylpiperidino) pyrimidine (3.3 raM).

100 ml of hexane was added to the mixture to form suspension. After the addition of hexane, the suspension was stirred for an hour. The solid substance thus formed was separated by filtration and 2.0 g of a white solid substance, a desired product, was obtained (yield 96%).

Melting point 177°–177.5° C.

¹ H-NMR spectrum (deuterochloroform, δ ppm) 1.4–2.0 (4H, m), 2.82 (3H, s), 2.6–3.2 (3H, m), 3.53 (3H, s), 4.2–4.6 (2H, m), 6.74 (1H, d, J=7Hz), 7.0–7.4 (7H, m), 7.72 (4H, s), 7.78 (2H, d, J=8Hz ), 8.46 ( 1 H, d, J=7Hz ), The physical properties of compounds produced by the same method as described above are shown in Table 3

TABLE 3

| Comp. No. | Yield (%) | Melting Point (° C.) | ¹H-NMR spectrum (CDCl₃ solution, δ ppm) |
|---|---|---|---|
| 104 | 50 | 147–149 | 2.35(3H, s), 3.13(2H, t, J=8Hz), 3.65(3H, s), 4.00(2H, t, J=8Hz), 6.02(1H, d, J=7Hz), 7.16(2H, d, J=8Hz), 6.8–7.6(9H, m), 7.86(2H, d, J=8Hz), 8.55(1H, d, J=7Hz) |
| 120 | 95 | 210–211 | 1.3–2.1(4H, m), 2.34(3H, s), 3.54(3H, s), 3.90(3H, s), 4.2–4.6(2H, m), 6.68(1H, d, J=7Hz), 7.14(2H, d, J=8Hz), 7.1–7.4(5H, m), 7.64(2H, d, J=8Hz), 7.80(2H, d, J=8Hz), 8.12(2H, d, J=8Hz), 8.47(1H, d, J=7Hz) |
| 128 | 93 | 168–169 | 1.4–2.1(4H, m), 2.38(3H, s), 2.6–3.3(3H, m), 3.57(3H, s), 4.2–4.6(2H, m), 6.86(1H, d, J=7Hz), 7.18(2H, d, J=8Hz), 7.1–7.4(5H, m), 7.78(4H, s), 7.80(2H, d, J=8Hz) 8.54(1H, d, J=7Hz) |
| 136 | 85 | 208–208.5 | 1.3–2.1(4H, m), 2.36(3H, s), 2.6–3.2(3H, m), 3.58(3H, s), 4.1–4.6(2H, m), 6.88(1H, d, J=7Hz), 7.14(2H, d, J=8Hz), 7.1–7.4(5H, m), 7.74(2H, d, J=8Hz), 7.84(2H, d, J=8Hz), 8.09(2H, d, J=8Hz), 8.54(1H, d, J=7Hz) |
| 144 | 88 | 175–177 | 1.2–2.0(4H, m), 2.35(3H, s), 2.5–3.2(3H, m), 3.64(3H, s), 4.3–4.5(2H, m), 6.62(1H, d, J=7Hz), 7.16(2H, d, J=8Hz), 7.1–8.2(12H, m), 7.80(2H, d, J=8Hz), 8.38(1H, J=7Hz) |
| 152 | 79 | 162–164 | 1.2–2.1(4H,m), 2.36(3H, s), 2.5–3.4(3H, m), 3.54(3H, s), 4.3–4.6(2H, m), 6.74(1H, d, J=7Hz), 7.14(2H, d, J=8Hz), 7.1–7.4(5H, m), 7.74(2H, d, J=8Hz), 7.78(2H, d, J=7Hz), 8.00(2H, d, J=8Hz), 8.30(1H, d, J=7hz), 10.1(1H, s) |
| 160 | 74 | 143–145 | 1.6–3.2(23H, m), 3.29(3H,s), 4.72(2H, m), 6.22(1H, d, J=7Hz), 7.20(5H, m), 8.24(1H, d, J=7Hz), |
| 168 | 72 | 135–140 | [CDCl₃-CD₃OD] 1.2–2.0(3H, m), 2.35(3H, s), 2.5–3.4(4H, m), 3.54(3H, s), 3.85(2H, m), 6,88(1H, d, J=7Hz), 7.0–8.3(9H, m) |
| 176 | 84 | 180–182 | 1.5–2.0(m, 4H), 2.28(s, 3H), 2.52(s, 3H), 3.47(s, 3H), 2.6–3.2(m, 3H), 4.2–4.6(m ,2H), 6.64(d, 1H, J=7Hz), 6.9–8.0(m, 13H), 8.36(d, 1H, J=7Hz) |
| 184 | 100 | 66–69 | 2.35(3H, s), 3.69(3H, s), 4.16(2H, s), 4.80(2H, s), 6.64(1H, d, J=7Hz), 7.14(2H, d, J=8Hz), 7.2–7.7(9H, m), 7.84(2H, d, J=8Hz), 8.58(1H, d, J=7Hz) |
| 272 | 93 | 196–197 | 1.74(6H, br.s), 1.9–2.4(2H, m), 2.40(3H, s), 2.6–2.9(2H, m), 3.86(4H, br.s), 4.06(2H, t, J=8Hz), 7.18(2H, d, J=8Hz), 7.82(2H, d, J=8Hz), 7.86(1H, d, J=7Hz), 8.38(1H, d, J=7Hz), |
| 280 | 73 | 177–178 | 1.5–2.5(5H, m), 2.37(3H, s), |

TABLE 3-continued

| Comp. No. | Yield (%) | Melting Point (° C.) | $^1$H-NMR spectrum (CDCl$_3$ solution, δ ppm) |
|---|---|---|---|
| | | | 2.6–3.4(6H, m), 4.07(2H, t, J=8Hz), 4.80(2H, br.d, J=12Hz), 7.16(2H, d, J=8Hz), 7.28(5H, s), 7.82(2H, d, J=7Hz), 7.90(2H, d, J=8Hz), 8.44(2H, d, J=7Hz) |
| 304 | 90 | 186–188 | 0.97(3H, d, J=7Hz), 1.0–2.3(7H, m), 2.36(3H, s), 2.6–3.3(4H, m), 4.03(2H, t, J=7Hz), 4.56(2H, m), 7.16(2H, d, J=7Hz), 7.80(3H, m), 8.35(1H, d, J=7Hz) |
| 312 | 92 | 152–154 | 0.91(3H, t, J=7Hz), 1.0–2.3(11H, m), 2.36(3H, s), 2.72(2H, t, J=7Hz), 3.06(2H, m), 4.03(2H, t, J=7Hz), 4.57(2H, m), 7.16(2H, d, J=7Hz), 7.80(3H, m), 8.34(1H, d, J=7Hz) |

Example 3

4-(N-formylpiperazino)-2-piperidino pyrimidine maleate (compound No. 224)

30 ml of ethyl acetate containing 0.42 g of maleic acid (3.6 mM) was added to 10ml of ethyl acetate containing 1.0 g of 4-(N-formylpiperazino)-2-piperidinopyrimidine (3.6 mM) at room temperature. The mixture was then stirred for an hour and concentrated under reduced pressure. Ether was added to the concentrate to crystalize and the crystal was resuspended. The solid substance thus formed was separated by filtration and 1.38 g of a white solid substance, a desired product, was obtained (yield 97%). Melting point 124°–126° C.

$^1$H-NMR spectrum (deuterochloroform, δ ppm) 1.76 (6H, br. s), 3.5–4.1 (12H, m), 6.18 (1H, d, J=7Hz), 6.31 (2H, s), 8.00 (1H, d, J=7Hz), 8.12 (1H, s)

The physical properties of compounds produced by the same method as described above are shown in Table 4.

TABLE 4

| Comp. No. | Yield (%) | Melting Point (°C.) | $^1$H-NMR spectrum (CDCl$_3$ solution, δppm) |
|---|---|---|---|
| 192 | 93 | 121–123 | 1.2–1.8(6H, m), 3.52(s, 3H), 3.2–3.7(4H, m), 3.95(s, 3H), 6.35(s, 2H), 6.60(d, 1H, J=7Hz), 7.60(d, 2H, J=7Hz), 8.08(d, 2H, J=7Hz), 8.22(d, 1H, J=7Hz), 11.6(br, 2H) |
| 200 | 81 | 101–103 | 1.2–1.8(m, 6H), 3.51(s, 3H), 3.2–3.7(m, 4H), 6.36(s, 2H), 6.72(1H, d, J=7Hz), 7.65(d, 2H, J=7Hz), 8.04(d, 2H, J=7Hz), 8.26(d, 1H, J=7Hz), 9.99(s, 1H) |
| 208 | 93 | 169–171 | 1.4–2.0(m, 6H), 2.41(s, 3H), 3.45(s, 3H), 3.2–3.7(m, 4H), 6.61(d, 1H, J=7Hz), 8.78(d, 1H, J=7Hz), 7.0–7.6(m, 4H), 6.40(s, 2H) |
| 216 | 78 | 83–84 | 2.43(3H, s), 2.72(4H, m), 3.46(3H, s), 4.15(4H, m), 6.40(2H, s), 7.22(1H, d, J=7Hz), 8.30(1H, d, J=7Hz) |
| 232 | 92 | 162–163 | 1.72(6H, br, s), 3.82(12H, br, s), 6.14(1H, d, J=7Hz), 6.34(2H, s), 7.50(5H, s), 8.10(1H, s) |
| 240 | 93 | 123–124 | 1.74(6H, br, s), 2.20(3H, s), 3.80(12H, br, s), 6.16(1H, d, J=7Hz), 6.32(2H, s), 8.16(1H, d, J=7Hz) |
| 248 | 90 | 97–100 | 1.5–2.3(4H, m), 2.6–3.5(3H, m), 3.82(8H, br, s), 4.70(2H, br, d, J=8Hz), 6.18(1H, d, J=7Hz), 7.1–7.4(5H, m), 7.46(5H, s), 8.14(1H, d, J=7Hz), 6.30(2H, s) |
| 256 | 93 | 149–151 | 1.6–2.2(4H, m), 2.20(3H, s), 2.8–3.5(3H, m), 3.80(8H, br, s), 4.72(2H, br, d, J=12Hz), 6.10(1H, d, J=7Hz), 6.33(2H, s), 7.1–7.5(5H, m), 8.16(1H, d, J=7Hz) |
| 264 | 58 | 78–81 | 1.5–2.2(4H, m), 2.6–3.3(3H, m) 3.52(3H, s), 4.68(2H, br, d, J=12Hz)6.24(1H, d, J=7Hz), 6.34(2H, s), 6.90(2H, d, J=8Hz), 7.2–7.4(5H, m), 7.50(2H, d, J=8Hz), 7.96(1H, d, J=7Hz) |
| 273 | 88 | 163–164 | 1.73(6H, m), 1.9–2.4(2H, m) 2.74(2H, t, J=7Hz), 3.92(4H, m), 4.07(2H, t, J=7Hz), 6.16(2H, s), 7.84(2H, d, J=7Hz), 8.34(1H, d, J=7Hz) |

Example 4

4-(2-oxopyrrolidino)-2-(4-phenylpiperidino) pyrimidine (compound No. 276) P 0.5 g of 4-chloro-2-(4-phenylpiperidino) pyrimidine (1.8 mM), 0.38 g of 4-amino butyric acid (3.7 mM) and 0.25 g of potassium carbonate (1.8 mM) were added to 30 ml of n-butanol. The mixture was heated at 120° C. for 6 hours and concentrated under reduced pressure. To the residue, chloroform and water were added for extraction. The organic layer was concentrated under reduced pressure. The concentrate was purified by a silca gel chromatography [developing solvent; methanol: methylene chloride (1:1)] to give 0.4 g of 4-(3-carboxylpropylamino)-2-(4-phenylpiperidino) pyrimidine (yield 66%). 0.4 g of 4-(3-carboxyl propylamino)-2-(4-phenylpiperidino) pyrimidine was dissolved in 10 ml of chloroform. 1 ml of thionyl chloride was added to the solution. The mixture was stirred at room temperature for 5 hours. Sodium carbonate solution was added to the mixture. The organic layer was separated and concentrated under reduced pressure. 0.19 g of white solid sobstance, a desired product, was obtained (yield 50%).

Melting point 177°–178° C.

$^1$H-NMR spectrum (deuterochloroform, δ ppm) 1.6–2.3 (5H, m), 2.4–4.2 (6H, m), 4.07 (2H, t, J=8Hz), 4.90 (2H, br.d, J=12Hz), 7.1–7.4 (5H, m), 7.56 (1H, d, J=7Hz), 8.24 (1H, d, J=7Hz)

The physical properties of compounds produced by the same method as described above are shown in Table 5.

TABLE 5

| Comp. No. | Yield (%) | Melting Point (°C.) | $^1$H-NMR spectrum (CDCl$_3$ solution, δppm) |
|---|---|---|---|
| 300 | 52 | 109–111 | 0.96(3H, d, J=7Hz), 1.0–3.0(11H, m), 4.03(2H, t, J=7Hz), 4.66(2H, m), 7.50(1H, d, J=6Hz), 8.18(1H, d, J=6Hz) |
| 308 | 50 | 93–98 | 0.8–3.0(16H, m), 4.04(2H, t, J=7Hz), 4.68(2H, m), 7.50(1H, d, J=5Hz), 8.18(1H, d, J=5Hz) |
| 316 | 93 | 153–155 | 1.85–1.30(6H, m), 2.64(2H, t, J=7Hz), 3.56(4H, m), 4.07(2H, t, J=7Hz), 7.54(1H, d, J=6Hz), 8.22(1H, d, J=6Hz) |
| 324 | 91 | oil | 1.18(3H, d, J=7Hz), 1.65(6H, m), 2.18(2H, m), 2.64(2H, t, J=7Hz), 2.92(1H, m), 4.04(2H, t, J=7Hz), 4.40–5.10(2H, m), 7.50(1H, d, |

TABLE 5-continued

| Comp. No. | Yield (%) | Melting Point (°C.) | $^1$H-NMR spectrum (CDCl$_3$ solution, δppm) |
|---|---|---|---|
| 332 | 95 | 93–94 | J=6Hz), 8.20(1H, d, J=6Hz) 0.94(3H, d, J=7Hz), 1.20–3.00(11H, m), 4.04(2H, t, J=7Hz), 4.54(2H, m), 7.50(1H, d, J=6Hz), 8.20(1H, d, J=6Hz) |
| 340 | 96 | 93–96 | 0.94(6H, d, J=7Hz), 1.40–3.60(10H, m), 4.03(2H, t, J=7Hz), 4.66(2H, m), 7.48(1H, d, J=6Hz), 8.19(1H, d, J=6Hz) |
| 348 | 61 | 135–137 | 2.12(2H, m), 2.65(2H, t, J=7Hz), 2.92(2H, t, J=7Hz), 4.03(2H, t, J=7Hz), 4.09(2H, t, J=7Hz), 4.88(2H, s), 7.18(4H, m), 7.58(1H, d, J=6Hz), 8.25(1H, d, J=6Hz) |
| 356 | 43 | 127–129 | 2.08(4H, m), 2.64(2H, t, J=7Hz), 2.80(2H, t, J=7Hz), 4.00(4H, m), 7.07(3H, m), 7.72(1H, d, J=6Hz), 7.76(1H, m), 8.30(1H, d, J=6Hz) |
| 364 | 82 | 110–112 | 1.04–2.96(13H, m), 4.02(2H, t, J=7Hz), 4.70(2H, m), 7.24(5H, m), 7.50(1H, d, J=6Hz), 8.19(1H, d, J=6Hz) |
| 372 | 95 | 81–83 | 2.27(3H, t, J=7Hz), 1.50–3.20(11H, m), 4.03(2H, t, J=7Hz), 4.14(2H, q, J=7Hz), 4.60(2H, m), 7.54(1H, d, J=6Hz), 8.20(1H, d, J=6Hz) |
| 380 | 67 | 141–143 | 2.10(2H, m), 2.64(2H, t, J=7Hz), 2.92(4H, m), 3.76(4H, m), 4.03(2H, t, J=7Hz), 7.55(1H, d, J=6Hz), 8.20(1H, d, J=6Hz) |
| 388 | 83 | 140–143 | 2.10(2H, t, J=7Hz), 2.65(2H, t, J=7Hz), 3.76(8H, s), 4.03(2H, t, J=7Hz), 7.61(1H, d, J=6Hz), 8.22(1H, d, J=6Hz) |
| 396 | 85 | 118–120 | 2.10(2H, m), 2.64(6H, m) 4.10(6H, m), 7.57(1H, d, J=6Hz), 8.21(1H, d, J=6Hz) |
| 404 | 80 | 128–129 | 2.10(2H, m), 2.35(3H, s), 2.46(4H, m), 2.65(2H, t, J=7Hz), 3.82(4H, m), 4.04(2H, t, J=7Hz), 7.57(1H, d, J=6Hz), 8.22(1H, d, J=6Hz) |
| 412 | 59 | 182–185 | 2.09(2H, m), 2.63(2H, t, J=7Hz), 3.20(4H, m), 3.96(6H, m), 6.92(3H, m), 7.22(2H, m), 7.64(1H, d, J=6Hz), 8.18(1H, d, J=6Hz) |
| 420 | 95 | 104–107 | 2.08(2H, m), 2.55(6H, m), 3.55(2H, s), 3.79(4H, m), 4.02(2H, t, J=7Hz), 7.33(5H, m), 7.55(1H, d, J=6Hz), 8.21(1H, d, J=6Hz) |
| 428 | 96 | 115–118 | 2.10(2H, m), 2.64(2H, t, J=7Hz), 3.16(6H, s), 4.06(2H, t, J=7Hz), 7.52(1H, d, J=6Hz), 8.21(1H, d, J=6Hz) |
| 436 | 48 | oil | 0.94(6H, t, J=7Hz), 1.2–1.8(8H, m), 2.08(2H, m), 2.62(2H, t, J=7Hz), 3.50(4H, t, J=7Hz), 4.00(2H, t, J=7Hz), 7.42(1H, d, J=6Hz), 8.14(1H, d, J=6Hz) |
| 268 | 70 | — | 1.68(6H, br, s), 1.9–2.4(2H, m), 2.4–2.6(2H, m), 3.74(4H, br, s), 4.07(2H, t, J=8Hz), 7.52(1H, d, J=7Hz), 8.22(1H, d, J=7Hz) |

Example 5

4-(2-oxopyrrolidino)-2-(4-piperidino) pyrimidine hydrochloride (compound No.274)

1.25 g of concentrated hydrochloric acid was added to 50 ml of methanol solution containing 3.05 g of 4-(2-oxopyrrolidino)-2-(4-piperidino) pyrimidine ( 12.4 mM) at room temperature. The mixture was stirred for an hour and concentrated under reduced pressure. Ethyl acetate was added to the concentrate for crystallization and the mixture was filtered to give 3.26 g of a white solid substance, a desired product (yield 90%).

Melting point: 260°–262° C. (dec.)

$^1$H-NMR spectrum (deuterochloroform, δ ppm) 1.75 (6H, m), 2.20 (2H, m), 2.75 (2H, t, J=7Hz), 3.98 (4H, m), 4.06 (2H, t, J=7Hz), 7.86 (1H, d, J=7Hz), 8.16 (1H, d, J=7Hz)

The physical properties of compounds produced by the same method as described above are shown in Table 6.

TABLE 6

| Comp. No. | Yield (%) | Melting Point (°C.) | $^1$H-NMR spectrum (CDCl$_3$ solution, δppm) |
|---|---|---|---|
| 320 | 95 | 263–266 (decomposition) | 2.12(6H, m), 2.76(2H, t, J=7Hz), 3.56–4.20(6H, m), 7.90(1H, d, J=7Hz), 8.18(1H, d, J=7Hz) |
| 328 | 93 | 161–164 | 1.34(3H, d, J=7Hz), 1.74(6H, m), 2.20(2H, m), 2.75(2H, t, J=7Hz), 3.24(1H, m), 4.08(2H, t, J=7Hz), 4.50–5.20(2H, m), 7.88(1H, d, J=7Hz), 8.22(1H, d, J=7Hz) |
| 336 | 84 | 213–217 (decomposition) | 1.04(3H, d, J=7Hz), 1.20–3.40(11H, m), 4.07(2H, t, J=7Hz), 4.66(2H, m), 7.86(1H, d, J=7Hz), 8.17(1H, d, J=7Hz) |
| 344 | 98 | 178–180 | 1.04(6H, d, J=7Hz), 1.40–3.80(10H, m), 4.06(2H, t, J=7Hz), 4.80(2H, m), 7.85(1H, d, J=7Hz), 8.18(1H, d, J=7Hz) |
| 352 | 84 | 158–163 | 2.21(2H, m), 2.74(2H, t, J=7Hz), 3.06(2H, m), 4.10(4H, m), 4.8–5.3(2H, m), 7.18(4H, m), 7.88(1H, d, J=7Hz), 8.18(1H, d, J=7Hz) |
| 360 | 97 | 140–145 | 2.18(4H, m), 2.72(4H, m), 3.87(2H, t, J=7Hz), 4.26(2H, t, J=7Hz), 7.20(3H, m), 7.48(1H, m), 8.06(1H, d, J=7Hz), 8.40(1H, d, J=7Hz) |
| 368 | 81 | 150–155 | 1.1–3.3(13H, m), 4.01(2H, t, J=7Hz), 4.80(2H, m), 7.19(5H, m), 7.81(1H, d, J=7Hz), 8.12(1H, d, J=7Hz) |
| 376 | 87 | 143–146 | 1.27(3H, t, J=7Hz), 1.6–2.7(7H, m), 2.74(2H, t, J=7Hz), 3.47(2H, m), 4.04(2H, t, J=7Hz), 4.15(2H, q, J=7Hz), 7.87(1H, d, J=7Hz), 8.15(1H, d, J=7Hz) |
| 384 | 98 | 285–289 (decomposition) | [CCDCl$_3$—CD$_3$OD] 1.18(2H, m), 2.71(2H, t, J=7Hz), 3.32(4H, m), 4.12(6H, m), 7.79(1H, d, J=7Hz), 8.20(1H, d, J=7Hz) |
| 392 | 87 | 169–173 | 2.23(2H, m), 2.78(2H, t, J=7Hz), 3.70–4.40(10H, m), 7.96(1H, d, J=7Hz), 8.20(1H, d, J=7Hz) |
| 400 | 85 | 172–176 | [CDCl$_3$—CD$_3$OD] 2.22(2H, m), 2.80(6H, m), 4.08(2H, t, J=7Hz), 4.28(4H, m), 7.96(1H, d, J=7Hz), 8.18(1H, d, J=7Hz) |
| 408 | 96 | 266–270 | [CDCl$_3$—CD$_3$OD] 2.08(2H, m), 2.68(2H, t, J=7Hz), 2.90(3H, s), 3.1–4.9(10H, m), 7.68(1H, d, J=7Hz), 8.23(1H, d, J=7Hz) |
| 416 | 60 | 187–189 | [CDCl$_3$—CD$_3$OD] 2.21(2H, m), 2.76(2H, t, J=7Hz), 3.7–4.6(10H, m), 7.43(3H, m), 7.69(2H, m), 7.98(1H, d, J=7Hz), 8.10(1H, d, J=7Hz) |
| 424 | 96 | 262–266 | 2.12(2H, m), 2.66(2H, t, J=7Hz), 2.80–4.90(12H, m), 7.46(3H, m), 7.64(2H, m), 7.70(1H, d, J=7Hz), 8.21(1H, d, J=7Hz) |
| 432 | 97 | 205–210 | 2.20(2H, m), 2.74(2H, t, J=7Hz), 3.30(3H, br, s), 3.50(3H, br, s), 4.07(2H, t, J=7Hz), 7.86(1H, d, J=7Hz), 8.16(1H, d, J=7Hz) |
| 440 | 64 | 127–127 | 0.96(6H, t, J=7Hz), 1.2–1.9(8H, m), |

TABLE 6-continued

| Comp. No. | Yield (%) | Melting Point (°C.) | $^1$H-NMR spectrum (CDCl$_3$ solution, δppm) |
|---|---|---|---|
| | | | 2.18(2H, m), 2.72(2H, t, J=7Hz), 3.58(2H, t, J=7Hz), 3.82(2H, t, J=7Hz), 4.02(2H, t, J=7Hz), 7.82(1H, d, J=7Hz), 8.16(1H, d, J=7Hz) |

Example 1B

Tablets each containing 10 mg of an active ingredient were prepared by the following procedure.

| | Per tablet |
|---|---|
| Active ingredient | 10 mg |
| Corn starch | 55 mg |
| Crystalline cellulose | 35 mg |
| Polyvinyl pyrrolidone (as 10% aqueous solution | 5 mg |
| Carboxymethyl cellulose calcium | 10 mg |
| Magnesium stearate | 4 mg |
| Talc | 1 mg |
| Total | 120 mg |

The active ingredient, corn starch and crystalline cellulose were passed through an 80-mesh sieve and thoroughly mixed. The mixed powder was granulated together with the polyvinyl pyrrolidone solution, and passed through an 18-mesh sieve. The resulting granules were dried at 50° to 60° C. and again passed through an 18-mesh sieve to adjust their sizes. The carboxymethyl cellulose calcium, magnesium stearate and talc which had been passed through an 80-mesh sieve, were added to the granules. They were mixed and tableted by a tableting machine to produce tablets each having a weight of 120 mg.

Example 2B

Tablets each containing 200 mg of an active ingredient were produced by the following procedure.

| | Per tablet |
|---|---|
| Active ingredient | 200 mg |
| Corn starch | 50 mg |
| Crystalline cellulose | 42 mg |
| Silicic anhydride | 7 mg |
| Magnesium stearate | 1 mg |
| Total | 300 mg |

The above components were passed through an 80-mesh sieve and thoroughly mixed. The resulting mixed powder was compression-molded to produce tablets each having a weight of 300 mg.

Example 3 B

Capsules each containing 100 mg of an active ingredient were produced by the following procedure.

| | Per capsule |
|---|---|
| Active ingredient | 100 mg |
| Corn Starch | 40 mg |
| Lactose | 5 mg |
| Magnesium stearate | 5 mg |
| Total | 150 mg |

The above components were mixed, passed through an 80-mesh sieve, and thoroughly mixed. The resulting mixed powder was filled into capsules in an amount of 150 mg for each.

Example 4B

Injectable preparations in vials each containing 5 mg of an active ingredient were produced by the following procedure.

| | Per vial |
|---|---|
| Active ingredient | 5 mg |
| Mannitol | 50 mg |

Just prior to use, these compounds were dissolved in 1 ml of distilled water for injection, and administered.

Example 5B

Injectable preparations in ampoules each containing 50 mg of an active ingredients were produced in accordance with the following recipe.

| | Per ampoule |
|---|---|
| Active ingredient | 50 mg |
| Sodium chloride | 18 mg |
| Distilled water for injection | proper amount |
| Total | 2 ml |

Example 6B

An adhesive patch containing 17.5 mg of an active ingredient was produced by the following procedure.

Ten parts of poly(ammonium acrylate) was dissolved in 60 parts of water. Two parts of glycerin diglycidyl ether was dissolved under heat in 10 parts of water. Furthermore, 10 parts of polyethylene glycol (grade 400) 10 parts of water and I part of an active ingredient were stirred to form, a solution. While the aqueous solution of poly(ammonium acrylate) was stirred, the aqueous solution of glycerin diglycidyl ether and the solution containing the active ingredient, polyethylene glycol and water were added and mixed. The resulting solution for hydrogel was coated on a pliable plastic film so that the rate of the active ingredient was 0.5 mg per cm$^2$. The surface was covered with releasing paper and cut to a size of 35 cm$^2$ to form an adhesive patch.

Example 7B

An adhesive patch containing 10 mg of an active ingredient was produced by the following procedure.

An aqueous sol prepared from 100 parts of poly (sodium acrylate), 100 parts of glycerin, 150 parts of water, 0.2 part of triepoxypropyl isocyanurate, 100 parts of ethanol, 25 parts of isopropyl myristate, 25 parts of propylene glycol and 15 parts of the active ingredient. The sol was then coated to a thickness of 100 micrometers on the non-moven fabric surface of a composite film composed of rayon non-woven fabric and a polyethylene film to form an adhesive layer containing the drug. The amount of the release aids (isopropyl myristate and propylene glycol) contained in this layer was about 20% by weight. The adhesive layer was then crosslinked at 25° C. for 24 hours, and a releasing film was bonded to the adhesive layer surface. The entire film was then cut into pieces each having an area of 35 cm$^2$.

The biological activities in vitro of the compounds of formula (I) on cells of the nervous system were tested. The cells tested were mouse neuroblastoma cell line neuro-2a (Dainippon Pharmaceutical Co., Ltd.) which have been established as the cells of the nervous system. The above nerve cells were grown in an incubator at 37° C. in the presence of 5% carbon dioxide gas exponentially, and the cultured for a certain period of time together with the compounds of formula (I). The results demonstrate that the compounds of formula (I) have nerve cell growth promoting activity and neurite formation and sprouting promoting activity which are markedly higher with a significance than a control, and are equal to, or higher than, isaxonine as a control drug (the compound described in Japanese Patent Publication No. 28548/1984).

The biological activities of the compounds of this invention on rat PC-12 pheochromocytoma cell line were also tested. When NGF is added to PC-12 cells, the neurites sprout, it was shown that when the compound of this invention is added at this time, the binding of NGF to the PC-12 cells and the up-take of NGF into the cells increased.

When the effect of the compounds of this invention on the binding of NGF to rabbit superior cervical ganglion was examined, they were found to promote the NGF binding.

Rats whose sciatic nerves were crushed were prepared as a model for peripheral nervous disorders and the effects of the compounds of this invention on it were tested. It was made clear that the compounds of the present invention have an effect of promoting recovery of the interdigit distance and the weight of the soleus muscle to normal values.

Rat and mouse models of central nervous disorders were prepared, and the pharmacological effects of the compounds of this invention were tested. Specifically, nigral dopamine cells of the rat brain were chemically destroyed by injecting a very small amount of 6-hydroxydopamine to induce motor imbalance. Two weeks later, dopamine cells of fatal brain were transplanted in the eaudate nucleus into the lesioned side of the rat brain and an attempt was made to improve the motor trouble. Specifically, beginning on the day of transplantation, the compound of the invention was intraperitoneally administered every day over 2 weeks, and the activity of the compounds of the invention on the improvement of the motor imbalance and the growth of the transplanted cells was examined. It was found that the compounds of the invention have a promoting effect on the improvement of the motor trouble.

The forebrain fundus of animals was destroyed by ibotenic acid and the like and then the compound of the present invention was administered to the animals. An amount of acetyl choline release and choline acetyl transferase activity of various sites in the cortex of cerebrum were tested. It was found that the compounds of the invention have a improved effect on them.

Rats and mice having a nerve trouble by mercury poisoning were prepared and the activity of the compounds of the invention was tested. The compounds were found to have a promoting effect on the improvement of the condition and recovery to a normal condition, a curative effect on chemicals-induced disorders and an effect of improving and recovering learning and memory.

Thus, it has been made clear that the compounds of this invention are useful as agents for improving or curing various neurological diseases of mammals, such as troubles in peripheral and central nerves, and also as agents for improving learning and memory.

Various types of neuropathy including, for example, various peripheral nerve disorders accompanied by motorgenie, sensory or objective flex retardation, and alcohol-induced or drug-induced, diabetic and metabolic, or idiopathic peripheral nerve disorders, including traumatic, inflammatory or immunological nerve root lesions may be cited as such neurological diseases. More specific examples include facial palsy, sciatic nerve paralysis, spinal muscular atrophy, muscular dystrophy, myasthenia gravis, multiple sclerosis, amyotrophic lateral sclerosis, acute disseminated cerebromyelitis, Guillan-Barre syndrome, postvaccinal encephalomyelitis, SMON disease, dementia, Alzheimer syndrome, a condition after cranial injury cerebral ischemia, sequela of cerebral infarction or cerebral hemorrhage, and rheumatism. These examples are not limitative.

By a toxicity test, the compounds of this invention were found to have only weak toxicity and side effect, and be used as safe and highly useful medicines.

Experimental Example 1

The effects of the compounds of this invention on neuroblastoma cells were examined by the following method.

Mouse neuro 2a cells in the logarithmic growth period in the Dulbecco's modified Eagle's medium [DMEM, containing 100 units/ml of penicillin G sodium and 100 micrograms/ml of streptomycin sulfate] containing 10% of FCS were seeded in a 48-well plate so that the number of cells was 1,000 cells/well, and cultured for one day in 0.25 ml of the culture fluid in each well in an incubator containing 5% of carbon dioxide gas in air at 37° C. The medium was replaced by a medium containing each antibiotics and FCS and the cells were further cultured for 24 hours. Then, a 4% aqueous glutaraldehyde solution in the same amount as a medium (0.25 ml) was added, and the culture was left to stand at room temperature for 2 hours to fix the cells. After washing with water, a 0.05% aqueous solution of methylene blue was added to stain the cells. Under a microscope, the number of cells containing outgrown neurites (cells having at least one neurite with a length of at least two times as large as the long diameter of the cell) was counted visually, and the proportion of these cells in the entire cells was calculated. The well was observed over 5 or more visual fields (at least 2% of the entire surface area of the well) continuous to the left and right from a mark put at the center of the well, and more than 200 cells was counted. One drug compound was used in 6 different concentrations at most, and three runs were conducted for each concentration. The results are expressed as a mean ±S.D., and the results are shown in Table 7.

Mouse neuroblastoma cells NS-20Y were similarly cultured in a dish coated with polyornithine, and the effects after 24 hours and 48 hours from the start of culturing are shown in Table 8.

TABLE 7

| Comp. No. | Ratio of the number of cells having neurites with a length of at least two times as large as the diameter of cells to the total number of cells (%) (concentration of compound solution, mM) |
|---|---|
| | Experiment 1 |

TABLE 7-continued

| Comp. No. | Ratio of the number of cells having neurites with a length of at least two times as large as the diameter of cells to the total number of cells (%) (concentration of compound solution, mM) |
|---|---|
| 104 | 3.4 ± 1.0 (0.03), 5.2 ± 2.9 (0.1) |
| 112 | 5.9 ± 0.9 (0.03), 43.3 ± 1.8 (0.1), 21.6 ± 3.3 (0.3), 10.0 ± 3.8 (1) |
| 120 | 12.6 ± 1.6 (0.03), 8.6 ± 5.5 (0.1) |
| 128 | 4.3 ± 1.6 (0.1), 4.8 ± 1.2 (0.3) |
| 136 | 5.2 ± 1.8 (0.03), 5.4 ± 1.7 (0.1) 10.3 ± 0.2 (0.3), 11.8 ± 1.4 (1) |
| Isaxonine | 23.0 ± 5.0 (10) |
| Control | 2.6 ± 1.5 |
| *Experiment 2* | |
| 144 | 5.1 ± 0.9 (0.01), 4.2 ± 0.6 (0.1) |
| 152 | 5.2 ± 0.4 (0.01), 16.5 ± 1.8 (0.03) |
| 160 | 5.1 ± 1.2 (0.03), 11.4 ± 1.3 (0.1), 23.5 ± 2.9 (0.3), 20.7 ± 2.7 (1) |
| 168 | 8.7 ± 2.0 (0.3), 14.6 ± 3.7 (1) |
| Isaxonine | 23.8 ± 4.7 (10) |
| Control | 2.4 ± 1.1 |
| *Experiment 3* | |
| 176 | 11.5 ± 2.1 (0.03), 18.4 ± 2.0 (0.01), 13.6 ± 0.9 (0.3), 14.8 ± 2.9 (1) |
| Isaxonine | 23.8 ± 4.7 (10) |
| Control | 3.0 ± 0.7 |
| *Experiment 4* | |
| 184 | 0.5 ± 0.8 (0.01), 0.9 ± 0.8 (0.1) |
| Isaxonine | 20.2 ± 0.8 (10) |
| Control | 2.6 ± 1.0 |
| *Experiment 5* | |
| 192 | 8.0 ± 1.3 (0.1), 13.8 ± 2.8 (0.3) |
| 200 | 5.8 ± 1.3 (0.1), 19.7 ± 3.1 (0.3) |
| 208 | 7.9 ± 0.6 (0.3), 12.7 ± 3.0 (1) |
| 216 | 4.4 ± 1.3 (0.3), 15.8 ± 3.2 (1) |
| 224 | 8.9 ± 1.5 (0.1), 21.4 ± 3.3 (0.3) |
| Isaxonine | 25.1 ± 2.8 (10) |
| Control | 5.5 ± 1.2 |
| *Experiment 6* | |
| 272 | 5.4 ± 0.4 (0.01), 10.5 ± 2.5 (0.1), 25.1 ± 2.7 (0.3), 20.4 ± 4.9 (1) |
| 280 | 7.1 ± 1.7 (0.01), 6.9 ± 1.4 (0.1), 7.5 ± 1.1 (0.3), 8.1 ± 6.3 (1) |
| Isaxonine | 16.0 ± 4.7 (10) |
| Control | 3.6 ± 0.5 |
| *Experiment 7* | |
| 273 | 5.3 ± 0.8 (0.01), 7.7 ± 2.0 (0.1), 24.0 ± 3.2 (0.3), 10.3 ± 4.0 (1) |
| 304 | 3.7 ± 1.2 (0.03), 6.8 ± 1.0 (0.1), 17.7 ± 2.9 (0.3) 16.3 ± 4.5 (1) |
| 312 | 3.8 ± 0.6 (0.01), 4.1 ± 1.2 (0.03) 12.7 ± 2.8 (0.1) |
| 274 | 25.8 ± 3.5 (0.3) |
| Isaxonine | 18.3 ± 2.4 (10) |
| Control | 2.4 ± 1.0 |
| *Experiment 8* | |
| 320 | 4.2 ± 1.9 (0.01), 4.2 ± 0.3 (0.1), 11.0 ± 0.8 (0.3), 10.7 ± 4.7 (1) |
| 328 | 3.9 ± 0.9 (0.01), 5.6 ± 1.7 (0.3), |
| 336 | 4.0 ± 1.0 (0.03), 5.7 ± 1.6 (0.1), 21.3 ± 3.0 (0.3), 21.2 ± 1.6 (1) |
| 344 | 5.6 ± 1.6 (0.01), 7.5 ± 3.3 (0.1) 10.4 ± 3.4 (0.3), 12.5 ± 1.3 (1) |
| 352 | 3.4 ± 0.1 (0.01), 4.2 ± 0.6 (0.3) |
| 360 | 4.8 ± 1.2 (0.03), 6.7 ± 0.8 (0.3) |
| 368 | 3.4 ± 0.3 (0.01), 14.4 ± 1.7 (0.1) |
| 376 | 3.4 ± 0.6 (0.01), 4.4 ± 0.8 (0.1), 6.0 ± 0.5 (0.3) |
| 384 | 4.1 ± 1.5 (0.01), 5.1 ± 2.1 (0.1), 8.3 ± 2.7 (0.3), 11.5 ± 1.3 (1) |
| 392 | 6.6 ± 2.2 (0.03), 5.6 ± 3.7 (0.1), 6.1 ± 4.0 (0.3) |
| 400 | 5.0 ± 0.1 (0.03), 6.3 ± 0.7 (0.1), 11.2 ± 1.5 (0.3), 12.1 ± 1.4 (1) |
| 408 | 4.9 ± 0.2 (0.03), 4.4 ± 0.2 (0.3) |
| 416 | 5.0 ± 1.9 (0.01), 4.4 ± 0.4 (0.1), 5.1 ± 1.2 (0.3) |
| 424 | 4.5 ± 2.4 (0.03), 5.9 ± 1.7 (0.1), 5.2 ± 2.5 (0.3) |
| 432 | 4.0 ± 2.2 (0.03), 4.2 ± 1.7 (0.1), 5.1 ± 1.2 (1) |
| 440 | 4.3 ± 0.8 (0.1) |
| Isaxonine | 18.8 ± 1.6 (10) |
| Control | 2.6 ± 0.7 |

TABLE 8

| Comp. | The number of cells in which neurites appeared/Total number of cells (concentration of compound solution) | |
|---|---|---|
| | 24 hour | 48 hour |
| 248 | 3/50 (0.2 mM) | 3/50 (0.1 mM) |
| Control | 1/50 | 2/50 |
| 256 | 3/50 (0.2 mM) | 4/50 (0.1 mM) |
| | 3/50 (0.1 mM) | 3/50 (0.2 mM) |
| Control | 0/50 | 0/50 |
| 264 | 3/50 (0.5 mM) | 3/50 (0.2 mM) |
| Control | 1/50 | 2/50 |
| 192 | 5/50 (0.5 mM) | 11/50 (0.5 mM) |
| | 5/50 (0.2 mM) | 7/50 (0.2 mM) |
| Control | 0/50 | 3/50 |
| 200 | 16/50 (0.5 mM) | 18/50 (0.5 mM) |
| | 8/50 (0.2 mM) | 11/50 (0.2 mM) |
| Control | 1/50 | 2/50 |
| 232 | 3/50 (0.2 mM) | 4/50 (0.1 mM) |
| Control | 0.50 | 2/50 |
| 240 | 5/50 (0.5 mM) | 6/50 (0.5 mM) |
| | 3/50 (0.1 mM) | 5/50 (0.2 mM) |
| Control | 1/50 | 2/50 |
| 216 | 3/50 (0.5 mM) | 4/50 (0.5 mM) |
| | 3/50 (0.2 mM) | 4/50 (0.5 mM) |
| Control | 0/50 | 1/50 |
| 104 | 4/50 (0.5 mM) | 3/50 (0.5 mM) |
| | 3/50 (0.2 mM) | 4/50 (0.2 mM) |
| Control | 2/50 | 1/50 |
| 112 | 3/50 (0.1 mM) | 2/50 (0.1 mM) |
| Control | 1/50 | 1/50 |
| 120 | 3/50 (0.2 mM) | 3/50 (0.2 mM) |
| Control | 0/50 | 2/50 |
| 128 | 3/50 (0.5 mM) | 4/50 (0.1 mM) |
| Control | 1/50 | 2/50 |
| 136 | 4/50 (0.5 mM) | 3/50 (0.2 mM) |
| Control | 2/50 | 2/50 |
| 208 | 3/50 (0.5 mM) | 6/50 (0.2 mM) |
| | 2/50 (0.2 mM) | 5/50 (0.5 mM) |
| Control | 1/50 | 2/50 |
| 160 | 2/50 (0.2 mM) | 3/50 (0.1 mM) |
| Control | 1/50 | 2/50 |
| 168 | 3/50 (0.2 mM) | 3/50 (0.5 mM) |
| Control | 1/50 | 2/50 |
| 176 | 4/50 (0.2 mM) | 4/50 (0.2 mM) |
| Control | 1/50 | 2/50 |
| 184 | 2/50 (0.1 mM) | 3/50 (0.1 mM) |
| Control | 1/50 | 2/50 |
| 144 | 3/50 (0.5 mM) | 4/50 (0.1 mM) |
| Control | 2/50 | 3/50 |
| 152 | 2/50 (0.1 mM) | 3/50 (0.1 mM) |
| Control | 1/50 | 0/50 |
| 224 | 2/50 (0.1 mM) | 3/50 (0.1 mM) |
| Control | 1/50 | 2/50 |
| 273 | 18/50 (0.5 mM) | 22/50 (0.5 mM) |
| | 15/50 (0.2 mM) | 16/50 (0.2 mM) |
| | 10/50 (0.1 mM) | 8/50 (0.1 mM) |
| Control | 1/50 | 2/50 |
| 304 | 16/50 (0.5 mM) | 17/50 (0.5 mM) |
| | 12/50 (0.2 mM) | 14/50 (0.2 mM) |
| | 8/50 (0.1 mM) | 7/50 (0.1 mM) |
| Control | 1/50 | 2/50 |
| 312 | 17/50 (0.5 mM) | 18/50 (0.5 mM) |
| | 13/50 (0.2 mM) | 13/50 (0.2 mM) |
| | 6/50 (0.1 mM) | 8/50 (0.1 mM) |
| Control | 0/50 | 1/50 |
| 274 | 6/50 (0.2 mM) | 6/50 (0.5 mM) |
| | 4/50 (0.1 mM) | 4/50 (0.2 mM) |
| Control | 1/50 | 1/50 |
| 320 | 6/50 (0.5 mM) | 3/50 (0.5 mM) |

TABLE 8-continued

| Comp. | The number of cells in which neurites appeared/Total number of cells (concentration of compound solution) | |
|---|---|---|
| | 24 hour | 48 hour |
| | 5/50 (0.1 mM) | |
| Control | 1/50 | 0/50 |
| 328 | 3/50 (0.1 mM) | 3/50 (0.1 mM) |
| Control | 1/50 | 1/50 |
| 336 | 3/50 (0.1 mM) | 5/50 (0.1 mM) |
| Control | 1/50 | 2/50 |
| 344 | 3/50 (0.1 mM) | 3/50 (0.1 mM) |
| Control | 1/50 | 1/50 |
| 352 | 5/50 (0.2 mM) | 3/50 (0.2 mM) |
| Control | 0/50 | 1/50 |
| 360 | 6/50 (0.5 mM) | 3/50 (0.1 mM) |
| | 5/50 (0.1 mM) | |
| Control | 1/50 | 1/50 |
| 368 | 6/50 (0.2 mM) | 2/50 (0.2 mM) |
| Control | 2/50 | 1/50 |
| 376 | 5/50 (0.2 mM) | 5/50 (0.2 mM) |
| Control | 1/50 | 1/50 |
| 384 | 14/50 (0.5 mM) | 17/50 (0.5 mM) |
| | 10/50 (0.2 mM) | 10/50 (0.2 mM) |
| Control | 1/50 | 3/50 |
| 392 | 15/50 (0.5 mM) | 21/50 (0.5 mM) |
| | 10/50 (0.2 mM) | 12/50 (0.2 mM) |
| Control | 1/50 | 3/50 |
| 400 | 9/50 (0.5 mM) | 13/50 (0.5 mM) |
| | 8/50 (0.2 mM) | 11/50 (0.2 mM) |
| Control | 0/50 | 2/50 |
| 408 | 10/50 (0.5 mM) | 11/50 (0.5 mM) |
| | 7/50 (0.2 mM) | 8/50 (0.2 mM) |
| Control | 2/50 | 1/50 |
| 416 | 9/50 (0.5 mM) | 9/50 (0.5 mM) |
| | 6/50 (0.2 mM) | 7/50 (0.2 mM) |
| Control | 2/50 | 2/50 |
| 424 | 5/50 (0.2 mM) | 2/50 (0.1 mM) |
| | 3/50 (0.1 mM) | |
| Control | 1/50 | 1/50 |
| 432 | 6/50 (0.5 mM) | 8/50 (0.5 mM) |
| | 6/50 (0.5 mM) | 7/50 (0.2 mM) |
| Control | 2/50 | 3/50 |
| 440 | 4/50 (0.5 mM) | 4/50 (0.1 mM) |
| | 3/50 (0.1 mM) | |
| Control | 2/50 | 1/50 |

Experimental example 2

Curative effect on rats with crushed sciatic nerves: The curing effect of the compound of the invention was tested on rats having crushed sciatic nerves as a model of peripheral nervous disorder using (1) a change in the action of the hind paw with the crushed sciatic nerves and (2) a change in the weight of the muscle as an index of the course of degeneration and regeneration of peripheral nerves.

In the experiment, male Wistar rats (6 weeks old), 10-15 per group, were used. The sciatic nerves were crushed by a method similar to the method of Yamatsu et al. (see Kiyomi Yamatsu, Takenori Kaneko, Akifumi Kitahara and Isao Ohkawa, Journal of Japanese Pharmacological Society, 72, 259–268 (1976) and the method of Hasegawa et al. (see Kazuo Hasegawa, Naoji Mikuni and Yutaka Sakai, Journal of Japanese Pharmacological Society, 7 4 721–734 (1978). Specifically, under anesthesia with pentobarbital (40 mg/kg, i.p.), the left side sciatic nerve was exposed at the femur and a given site was crushed with hemostat (2ram in width) for 30 seconds. After crushing, the operated site was immediately sitched. Vincristine, known to delay the regeneration of peripheral nerves, was administered intraperitoneally at 100 μg/kg per week.

Test compounds selected from the compounds of the invention were administered intraperitoneally or orally once a day from the day of operation to the 30th day. A group to which 0.9% saline was administered was used as control.

(1) Functional change in the hind paw with crushed nerves.

Twitch tension, a temporary tension accompanied by contraction of muscles controlled by electrical stimuli of motor nerves, reflects functional changes of nerves and muscles similar to those of interdigital distances described below.

Thirty days later, the twitch tension of rats was measured under anesthesia with chloral hydrate (400 mg/kg, i.p.) according to the method described by Kern et al., in J. Neurosci. Methods, 19: 259, 1987. After the hair of the hind paws of rats were shaved, the hind paws were coated with cardiocream. Electrodes with crocodile clips were attached to the skins of the hind paws. A cathode was attached to the rear portion of the greater trochanter and the anode was attached to the rear portion 1 cm distal from the cathode, and I cm toward its back. Rats were fixed with laying on their backs and their hind paws to be measured are fixed upright. One end of a 20-cm silk thread was tied to the distal joint of the third toe of the hind paw to be measured and at the other end to a tension transducer and an isotonic contraction of the bending muscle of the third toe was recorded on polygraph as electrically stimulated. An electric stimuli was carried out at 100 V for 1 millisecond at a square wave of 2 Hz. Static tension was 15–30 g and 10 stimuli were repeated 3 times at a 15-second interval. Contraction was represented by tension g. The recovery rate of contraction [left side/right side (%)] was calculated from the measurement of both hind paws. The test compounds were found to enhance the recovery of twich tension, which is an electrophysiological index, and to improve symptons.

The distance between digits was measured because this is a good index which functionally shows the degeneration and regeneration of the nerve and its change can be measured with the lapse of time.

According to the method of Hasegawa [Hasegawa, K., Experientia, 34, 750–751 ( 1978)], the distance between the first and fifth digits of the hind paw was measured and the ratio of a crushed-side distance to a normal-side distance was calculated.

The distance between the digits of the hind paw with crushed nerves was no more than 40% of that of the normal hind paw.

The recovery of the interdigital distance started 7–16 days later. Drug-administered groups had tendency of quicker recovery from 24th day to 30th day, that is a last day for measurment, compared to the controls. The results are shown in Table 9.

(2) Change in the weight of muscle

It is known that the removal of a nerve or its disorder causes atrophy of the muscle which is under its control, and the atrophy is gradually cured by re-control by the nerve. For this reason, a change in the weight of the muscle, which is quantitative, was selected as an index. 30 days after the operation, the soleus muscles of both sides of paws were measured under anesthesia. The ratio of the weight of the soleus muscle on the crushed side to that of normal side was calculated and expressed in percentage (%).

The results show that the test compounds are useful as improvers and therapeutic agents for the disorder of peripheral nerves.

TABLE 9

Rate of recovery of the interdigital distance*

| Dose mg/kg | Days after crush | | | | |
|---|---|---|---|---|---|
| | 7 | 14 | 16 | 18 | 20 |
| Control | 37.2 ± 3.7 | 39.1 ± 3.5 | 36.9 ± 3.8 | 41.1 ± 6.3 | 43.4 ± 10.7 |
| 7.5 | 42.6 ± 6.8 | 37.6 ± 3.5 | 38.4 ± 3.8 | 40.9 ± 6.2 | 45.6 ± 14.0 |
| 15 | 39.8 ± 5.2 | 38.2 ± 2.8 | 39.4 ± 2.5 | 40.5 ± 4.2 | 46.7 ± 7.3 |
| 30 | 38.8 ± 4.4 | 39.2 ± 3.4 | 38.3 ± 3.5 | 40.8 ± 4.5 | 43.8 ± 6.7 |

| Dose mg/kg | Days after crash | | | | |
|---|---|---|---|---|---|
| | 22 | 24 | 26 | 28 | 30 |
| Control | 49.6 ± 15.1 | 52.9 ± 19.2 | 56.3 ± 20.8 | 57.7 ± 21.9 | 63.0 ± 23.0 |
| 7.5 | 46.8 ± 13.2 | 48.2 ± 15.2 | 54.8 ± 18.3 | 66.9 ± 19.6 | 64.0 ± 21.2 |
| 15 | 50.0 ± 10.0 | 56.8 ± 17.8 | 62.2 ± 18.7 | 65.5 ± 19.8 | 70.1 ± 21.4 |
| 30 | 47.8 ± 11.5 | 57.0 ± 16.1 | 60.9 ± 18.8 | 68.6 = 17.1 | 73.6 ± 20.0 |

*Compound 274 is orally administered to a group of rats with the crushed sciatic nerve and the recovery of the interdigital distance is measured.
The ratio of the weight of the soleus muscle on the crushed side to that of normal side (%) in (1) and (2), Mean ± S.D. (n = 15)

Experimental Example 3

Promoting effect on the improvement of motor imbalance due to injury of the rat's brain cells by transplantaion of fetal cerebral cells Nigral dopaminergic nerve cells at the left side of the brain of 4-week old female Wistar rats (body weight 100 g) were lesioned by injecting a very small quantity of 6-hydroxydopamine. The rats showed a tendency to rotate spontaneously in a direction opposite to the lesioned side for several days, but no apparent abnormal action was observed after that. Upon administration of methamphethamine (5 mg/kg, i.p.) to the rats having the lesioned nigral dopaminergic nerve cells, they began rotational movement toward the lesioned side.

After two weeks from the destruction by the administration of the drug, portions of the truncus corporis callosi-containing dopamine cells. (i.e., substantia nigra and the tagmentum at the abdomen side) were cut from the brain of a fetal rat of 14 to 17 days of age, cut finely, and treated with trypsin. Then, the extracted tissues were incubated at 37° C. for 30 minutes, and the tissues were subjected to pipetting to form a suspension. Five microliters of the suspension was transplanted each into two sites of the eaudate nucleus of the lesioned side (10 microliters in total, about 105 cells).

Test compounds of the present invention was administered (i.p., or p.o.) over 14 days from the day of transplantation. The rotational movements induced by administration of methamphetamine were examined 2 weeks and 1 week before, and 2 weeks, 4 weeks, 6 weeks and 8 weeks after, the transplantation and the administration of the drug. The number of rotational movements within one minute was counted at intervals of 10 minutes after the administration of methamphetamine, and the total number of rotational movements counted six times was averaged to find a mean number of the rotational movements. The test compounds apparently reduced the number of rotational movements on each test day as compared to controls so that the test compounds are found to be useful as improvers and therapeutic agents for the disorders of the peripheral nerves.

Exprimental Examples 4

Improvement of learning and memory of mice with nerve disorder induced by mercury poisoning, and recovery effect.

Male Balb C strain mice, 7 weeks old, were first caused to learn at T-shaped maze three times in a week so that they run straight from a starting point to a safety area. Then, methylmercury chloride (MMC for short) was administered orally to 8 weeks old mice for 6 days in a dose of 6 mg/kg/day- A group of mice to which saline was administered in a dose of 0.1 ml/10 g/day was used as a control group. Beginning with the day next to the day of administering MMC, compounds of the present invention were intraperitoneally administered over 10 days. On the sixth day after administration of the drug (namely, on the 12th day after start of the experiment), learning of the T-shaped maze was resumed, and the running behaviour of the mice were observed. The number of mice which could be experimented in the T-shaped maze on the 10th and 1 1 th days after the resumption (21st and 22rid days after the start of the experiment) was counted and expressed as a denominator. The number of mice which ran to the safety area within 5 seconds at least 8 times out of ten trial runnings was counted and expressed as a numerator. The decrease in the number of the test animals was due to death by MMC poisoning. The time (seconds) required for the animals to run to the safety area was measured, and the mean±standard error (SE) was calculated.

The results demonstrate the effect of the compounds of the invention to improve learning and memory of the mouse and their recovery effect.

Experimental Example 5

The acute toxicity of the compounds of the invention was examined by the following method.

Male ddy-strain 5-week old mice, 4–6 per group, were used as experimental animals. Each of the compounds was dissolved or suspended in saline and administered perorally (p.o.) or intraperitoneally (i.p.), and the toxicity of the compound was assessed 24 hours after the administration. The results are shown in Table 10.

TABLE 10

Acute toxicity in mouse

| Comp. No. | Estimated $LD_{50}$ (mg/kg i.p.) |
|---|---|
| 104 | >1000 |
| 112 | >1000 |
| 120 | >1000 |
| 128 | >1000 |
| 136 | >1000 |
| 152 | >1000 |
| 160 | 500~1000 |
| 168 | >1000 |
| 176 | >1000 |
| 192 | 500~1000 |
| 200 | >1000 |
| 208 | >1000 |
| 216 | 500~1000 |
| 223 | >1000 |
| 232 | >1000 |
| 240 | >1000 |
| 248 | >1000 |
| 256 | >1000 |
| 264 | >1000 |
| 272 | 250~500 |
| 273 | >500 |
| 274 | 250~500 |

TABLE 10-continued

| | Acute toxicity in mouse |
|---|---|
| Comp. No. | Estimated $LD_{50}$ (mg/kg i.p.) |
| 280 | >1000 |
| 288 | >1000 |
| 296 | >1000 |
| 304 | >250~500 |
| 312 | >500 |
| 320 | >500 |
| 328 | 250~500 |
| 336 | 250~500 |
| 344 | 250~500 |
| 352 | >500 |
| 360 | >500 |
| 368 | >500 |
| 376 | >500 |
| 384 | >500 |
| 392 | >500 |
| 400 | >500 |
| 408 | >500 |
| 416 | >500 |
| 424 | >500 |
| 432 | >500 |
| 440 | >500 |

EFFECT OF THE INVENTION

The compounds of general formula (I) provided by this invention have a promoting effect on the proliferation of nerve cells and the formation and sprouting of neurites and a nerve regenerating effect and a motor function recovering effect in rats and mice having nerve disorders, and can be used suitably for improving and curing neurological diseases such as disorders of peripheral nerves or central nerves and dementia. They are expected to be used also suitably for the recovery, improving and curing of neurological diseases caused by disorder of nervous tissues and cells which have to do with perceptive and sensory functions and an autonomic function.

It has been found that the compounds of the invention have biological activities equal to, or higher than, those of isaxonine as a control as shown in Experimental Examples 1 to 4 and Tables 7 to 9. The toxicity of the compounds of this invention are generally weak as shown in Experimental Examples 5 and Table 10. Thus, the compounds of this invention are generally considered to be highly active and highly safe drugs and very useful with weak toxicity.

What is claimed is:

1. A pyrimidine compound represented by the following formula (I)

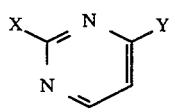  (I)

wherein
X is selected from the group consisting of

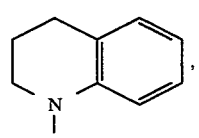  (a)

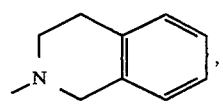  (b)

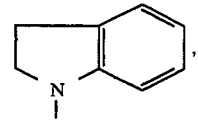  (c)

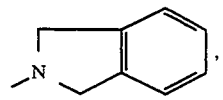  (d)

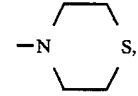  (e)

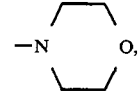  (f)

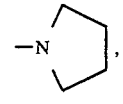  (g)

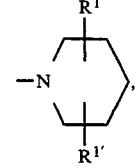  (h)

where $R^1$ and $R^{1'}$ may be the same or different and each represents a hydrogen atom, a lower alkyl group, a benzyl group, a phenyl group or a lower alkoxycarbonyl group,

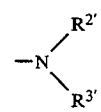  (i)

wherein $R^{2'}$ and $R^{3'}$ represent a lower alkyl group, and

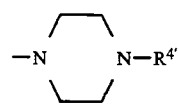  (j)

wherein $R^{4'}$ is a hydrogen atom, a lower alkyl group, a phenyl group or a benzyl group; and
Y represents

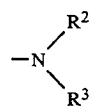  (a')

wherein $R^2$ is a hydrogen atom or a lower alkyl group,

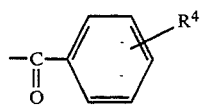

wherein $R^4$ is a hydrogen atom, a trifluoromethyl group, a hydroxyl group, a cyano group, a formyl group, a lower acyl group, a lower alkoxycarbonyl group or a fluorosulfonyl group

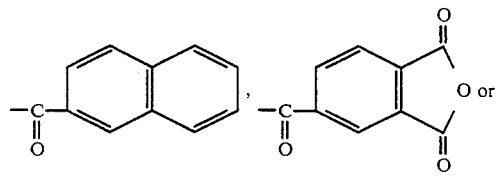

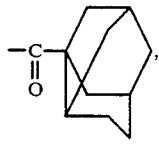

provided that, when Y is

and $R^3$ is a lower acyl group or

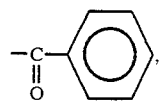

X is selected from the group consisting of

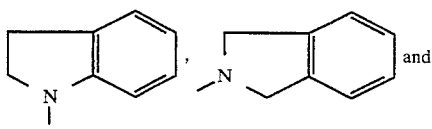

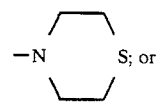

pharmaceutically acceptable salts thereof.

2. The compound according to claim 1, wherein the pharmaceutically acceptable salts are selected from the group consisting of hydrochloride, hydrobromide, sulfate, bisulfate, phosphate, acidic phosphate, acetate, maleate, fumarate, succinate, lactate, tartrate, benzoate, citrate, gluconate, glucanate, methanesulfonate, p-toluenesulfonate, naphthalenesulfonate and quaternary ammonium salts.

3. A therapeutic composition for neurological diseases comprising a therapeutically effective amount of a compound according to claim 1, as active ingredient, and a pharmaceutically acceptable carrier therefor.

4. The therapeutic composition according to claim 3, wherein the pharmaceutically acceptable salts are selected from the group consisting of hydrochloride, hydrobromide, sulfate, bisulfate, phosphate, acidic phosphate, acetate, maleate, fumarate, succinate, lactate, tartrate, benzoate, citrate, gluconate, glucanate, methanesulfonate, p-toluenesulfonate, naphthalene-sulfonate and quaternary ammonium salts.

* * * * *